United States Patent
Downey

(10) Patent No.: US 12,226,798 B2
(45) Date of Patent: *Feb. 18, 2025

(54) POWER CONSOLE FOR A SURGICAL TOOL THAT INCLUDES A TRANSFORMER WITH AN INTEGRATED CURRENT SOURCE FOR PRODUCING A MATCHED CURRENT TO OFFSET THE PARASITIC CURRENT

(71) Applicant: Stryker Corporation, Kalamazoo, MI (US)

(72) Inventor: Adam Darwin Downey, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/208,523

(22) Filed: Jun. 12, 2023

(65) Prior Publication Data

US 2023/0321689 A1 Oct. 12, 2023

Related U.S. Application Data

(63) Continuation of application No. 16/303,026, filed as application No. PCT/US2017/034437 on May 25, 2017, now Pat. No. 11,673,163.

(Continued)

(51) Int. Cl.
  B06B 1/02 (2006.01)
  A61B 17/32 (2006.01)
  (Continued)

(52) U.S. Cl.
  CPC .... B06B 1/0276 (2013.01); A61B 17/320068 (2013.01); B06B 1/0614 (2013.01);
  (Continued)

(58) Field of Classification Search
  CPC ............... B06B 1/0276; B06B 1/0614; A61B 17/320068
  See application file for complete search history.

(56) References Cited

U.S. PATENT DOCUMENTS

| | | | |
|---|---|---|---|
| 3,248,620 A * | 4/1966 | Haft | H01G 4/32 361/313 |
| 3,746,897 A | 7/1973 | Karatjas | |

(Continued)

FOREIGN PATENT DOCUMENTS

| | | |
|---|---|---|
| AU | 2010300943 B2 | 11/2013 |
| AU | 2013204307 B2 | 3/2015 |

(Continued)

OTHER PUBLICATIONS

English language abstract and machine-assisted English translation for CN 105099212 A extracted from espacenet.com database on Feb. 11, 2021, 13 pages.

(Continued)

*Primary Examiner* — Jue Zhang
*Assistant Examiner* — Afework S Demisse
(74) *Attorney, Agent, or Firm* — Howard & Howard Attorneys PLLC

(57) ABSTRACT

Control console for a powered surgical tool that includes a transformer with a secondary winding across which the tool drive signal is present. Also internal to the transformer is a matched current source that consists of a leakage control winding and a capacitor. The current sourced by the matched current at least partially cancels out leakage current that may be present.

21 Claims, 11 Drawing Sheets

Related U.S. Application Data

(60) Provisional application No. 62/343,433, filed on May 31, 2016.

(51) Int. Cl.
  *B06B 1/06* (2006.01)
  *H01F 27/30* (2006.01)
  *H03H 5/02* (2006.01)
  *A61B 17/00* (2006.01)
  *A61B 18/00* (2006.01)

(52) U.S. Cl.
  CPC .............. *H01F 27/306* (2013.01); *H03H 5/02* (2013.01); *A61B 2017/00199* (2013.01); *A61B 2017/00411* (2013.01); *A61B 2018/00869* (2013.01); *B06B 2201/76* (2013.01)

(56) References Cited

U.S. PATENT DOCUMENTS

| | | | |
|---|---|---|---|
| 3,889,166 A | 6/1975 | Scurlock | |
| 3,946,738 A | 3/1976 | Newton et al. | |
| 3,975,650 A | 8/1976 | Payne | |
| 4,094,320 A | 6/1978 | Newton et al. | |
| 4,231,372 A | 11/1980 | Newton | |
| 4,271,371 A | 6/1981 | Furuichi et al. | |
| 4,336,509 A | 6/1982 | Bernitz | |
| 4,437,746 A | 3/1984 | Ikemori | |
| 4,554,477 A | 11/1985 | Ratcliff | |
| 4,625,270 A | 11/1986 | Taylor | |
| 4,642,581 A | 2/1987 | Erickson | |
| 5,136,199 A | 8/1992 | Kawai | |
| 5,152,762 A | 10/1992 | McElhenney | |
| 5,318,563 A | 6/1994 | Malis et al. | |
| 5,372,596 A | 12/1994 | Klicek et al. | |
| 5,394,047 A | 2/1995 | Scharlack et al. | |
| 5,930,121 A | 7/1999 | Henry | |
| 6,245,063 B1 | 6/2001 | Uphoff | |
| 6,398,781 B1 | 6/2002 | Goble et al. | |
| 6,819,027 B2 | 11/2004 | Saraf | |
| 7,160,020 B2 | 1/2007 | Sand | |
| 7,794,414 B2 | 9/2010 | Rabiner et al. | |
| 7,857,783 B2 | 12/2010 | Kadziauskas et al. | |
| 8,115,366 B2 | 2/2012 | Hoffman et al. | |
| 8,197,502 B2 | 6/2012 | Smith et al. | |
| 8,236,020 B2 | 8/2012 | Smith et al. | |
| 8,439,416 B2 | 5/2013 | Lambarth et al. | |
| 8,475,446 B2 | 7/2013 | Daw et al. | |
| 8,551,088 B2 | 10/2013 | Falkenstein et al. | |
| 8,624,606 B2 | 1/2014 | Gilbert | |
| 8,669,809 B2 | 3/2014 | Ikriannikov et al. | |
| 8,864,205 B2 | 10/2014 | Lemire et al. | |
| 8,956,349 B2 | 2/2015 | Aldridge et al. | |
| 8,973,963 B2 | 3/2015 | Lambarth et al. | |
| 9,060,775 B2 | 6/2015 | Wiener et al. | |
| 9,072,539 B2 | 7/2015 | Messerly et al. | |
| 9,319,008 B2 | 4/2016 | Ikriannikov et al. | |
| 9,456,939 B2 | 10/2016 | Lambarth et al. | |
| 9,615,983 B2 | 4/2017 | Stryker et al. | |
| 10,022,567 B2 | 7/2018 | Messerly et al. | |
| 10,022,568 B2 | 7/2018 | Messerly et al. | |
| RE47,996 E | 5/2020 | Turner et al. | |
| 11,673,163 B2 | 6/2023 | Downey | |
| 2005/0212505 A1 | 9/2005 | Murray et al. | |
| 2005/0253536 A1 | 11/2005 | Oyama | |
| 2007/0247877 A1 | 10/2007 | Kwon et al. | |
| 2007/0249941 A1 | 10/2007 | Salehi et al. | |
| 2009/0088737 A1 | 4/2009 | Daw et al. | |
| 2010/0102672 A1 | 4/2010 | Hoffman et al. | |
| 2010/0125292 A1 | 5/2010 | Wiener et al. | |
| 2010/0318079 A1 | 12/2010 | McPherson et al. | |
| 2011/0087212 A1 | 4/2011 | Aldridge et al. | |
| 2011/0215807 A1 | 9/2011 | Misic et al. | |
| 2011/0241576 A1 | 10/2011 | Paschke | |
| 2012/0078139 A1 | 3/2012 | Aldridge et al. | |
| 2012/0172866 A1 | 7/2012 | Behnke, II | |
| 2012/0221031 A1 | 8/2012 | Smith et al. | |
| 2012/0265196 A1 | 10/2012 | Turner et al. | |
| 2013/0035679 A1 | 2/2013 | Orszulak | |
| 2013/0079609 A1 | 3/2013 | Besko | |
| 2013/0345695 A1 | 12/2013 | McPherson | |
| 2014/0049299 A1 | 2/2014 | Chu | |
| 2014/0080413 A1 | 3/2014 | Hayes et al. | |
| 2014/0139313 A1 | 5/2014 | Zhou et al. | |
| 2015/0098307 A1 | 4/2015 | Lei et al. | |
| 2015/0105767 A1* | 4/2015 | Johnson ............. A61B 18/1206 606/34 |
| 2016/0022348 A1 | 1/2016 | Bales, Jr. et al. | |
| 2016/0030104 A1 | 2/2016 | Gilbert et al. | |
| 2016/0302848 A1 | 10/2016 | Krapohl | |
| 2016/0367416 A1 | 12/2016 | Lambarth et al. | |
| 2017/0000542 A1 | 1/2017 | Yates et al. | |
| 2017/0027029 A1 | 1/2017 | Hu et al. | |
| 2017/0071621 A1 | 3/2017 | Downey et al. | |
| 2017/0086913 A1 | 3/2017 | Yates et al. | |
| 2017/0143369 A1 | 5/2017 | Downey et al. | |
| 2017/0146584 A1 | 5/2017 | Daw et al. | |
| 2017/0151011 A1 | 6/2017 | Brustad et al. | |
| 2018/0036030 A1 | 2/2018 | Pantano | |
| 2020/0384502 A1 | 12/2020 | Downey et al. | |

FOREIGN PATENT DOCUMENTS

| | | |
|---|---|---|
| CN | 1225757 A | 8/1999 |
| CN | 1586672 A | 3/2005 |
| CN | 101022246 A | 8/2007 |
| CN | 102332447 A | 1/2012 |
| CN | 105099212 A | 11/2015 |
| CN | 204767038 U | 11/2015 |
| CN | 206422702 U | 8/2017 |
| EP | 2283788 A1 | 2/2011 |
| EP | 2470140 A2 | 7/2012 |
| EP | 2537499 A2 | 12/2012 |
| EP | 2777577 A1 | 9/2014 |
| EP | 2895130 A1 | 7/2015 |
| EP | 3177217 A1 | 6/2017 |
| GB | 2090705 A | 7/1982 |
| GB | 2448585 A | 10/2008 |
| JP | S5853195 A | 3/1983 |
| JP | H04066301 A | 3/1992 |
| JP | H0747080 A | 2/1995 |
| JP | 2004364344 A | 12/2004 |
| JP | 5552167 B2 | 7/2014 |
| WO | 9804029 A1 | 1/1998 |
| WO | 2011041170 A2 | 4/2011 |
| WO | 2014043659 A1 | 3/2014 |
| WO | 2014122647 A1 | 8/2014 |
| WO | 2015021216 A1 | 2/2015 |
| WO | 2016022808 A1 | 2/2016 |
| WO | 2016183084 A1 | 11/2016 |
| WO | 2017011619 A1 | 1/2017 |
| WO | 2017106329 A1 | 6/2017 |
| WO | 2017210076 A2 | 12/2017 |

OTHER PUBLICATIONS

English language abstract and machine-assisted English translation for CN 1586672 A extracted from espacenet.com database on Feb. 11, 2021, 8 pages.

English language abstract and machine-assisted English translation for JPH 04-066301 A extracted from espacenet.com database on Mar. 17, 2023, 4 pages.

English language abstract and machine-assisted English translation for JPH 07-47080 A extracted from espacenet.com database on Mar. 17, 2023, 9 pages.

English language abstract for JP 5552167 extracted from espacenet.com database on Jan. 28, 2019, 2 pages.

Gentile, Ken, "Driving a Center-Tapped Transformer with a Balanced Current-Output DAC", Analog Devices, AN-912, Application Note, 2007, pp. 1-12.

International Search Report for Application No. PCT/US2016/031651 dated Oct. 10, 2016, 7 pages.

(56) References Cited

OTHER PUBLICATIONS

International Search Report for Application No. PCT/US2017/034437 Jan. 26, 2018, 4 pages.
International Search Report for Application No. PCT/US2018/0633775 dated Mar. 27, 2019, 5 pages.
Invitation to Pay Additional Fees—Communication Relating to the Results of the Partial International Search for Application No. PCT/US2017/034437 dated Nov. 3, 2017, 3 pages.
Machine-assisted English translation for JPS 58-53195 extracted from PAJ database on Dec. 6, 2017, 3 pages.
Svilanis, G., et al., "Power Amplifier for Ultrasonic Transducer Excitation", ISSN 1392-2114, ULTRAGARSAS, Nr. 1(58), 2006, pp. 30-36.
English language abstract and machine-assisted English translation for CN 204767038 U extracted from espacenet.com database on Jan. 3, 2024, 15 pages.
English language abstract and machine-assisted English translation for JP 2004-364344 A extracted from espacenet.com database on Jan. 3, 2024, 8 pages.
English language abstract for CN 1225757 A extracted from espacenet.com database on Apr. 3, 2024, 2 pages.
English language abstract and machine-assisted English translation for CN 102332447 A extracted from espacenet.com database on Apr. 3, 2024, 12 pages.
English language abstract and machine-assisted English translation for CN 101022246 A extracted from espacenet.com database on Aug. 14, 2024, 39 pages.
English language abstract and machine-assisted English translation for CN 206422702 U extracted from espacenet.com database on Jul. 23, 2024, 2 pages.

* cited by examiner

POWER CONSOLE FOR A SURGICAL TOOL THAT INCLUDES A TRANSFORMER WITH AN INTEGRATED CURRENT SOURCE FOR PRODUCING A MATCHED CURRENT TO OFFSET THE PARASITIC CURRENT

RELATED APPLICATIONS

This application is a continuation from U.S. Nonprovisional patent application Ser. No. 16/303,026, filed on Nov. 19, 2018, which is a U.S. National Stage of International Patent Application No. PCT/US2017/034437, filed on May 25, 2017, which claims the benefit of and priority to U.S. Provisional Patent Application Ser. No. 62/343,433, filed on May 31, 2016, the entire contents of each of which are hereby incorporated by reference in their entireties.

FIELD OF THE INVENTION

This invention relates generally to a power console that supplies drive signals to an electrically powered surgical tool. The power console of this invention includes a transformer with an internal matched current source. This current source produces a current matched to the parasitic current to minimize the leakage current.

BACKGROUND OF THE INVENTION

A powered surgical tool system generally can be considered to have three basic components. A control assembly produces drive signals that have characteristics necessary to actuate the second component of the system, the power generator. The power generator typically converts the electrical energy of the drive signals into another form of energy. The types of energy into which the electrical energy is converted include, mechanical energy, thermal energy (heat) and photonic (light) energy. The third component of the tool system is the energy applicator. The energy applicator receives the energy output by the power generator and applies this energy to the targeted tissue to perform a specific therapeutic task. Some tool systems are designed to apply electrical energy directed to the targeted tissue. In this type of system, the power generator is essentially the conductors over which the drive signals are applied to the exposed electrodes over which the current is sourced to the tissue. The electrodes function as the energy applicator.

An integral part of many surgical tool systems is the handpiece. At a minimum, the handpiece is the physical component designed to be held by the practitioner from which the energy applicator extends. Often the power generator is contained in the handpiece. One such surgical tool system so designed is an ultrasonic surgical tool system. The handpiece of this system includes a power generator that consists of one or more drivers. Each driver, in response to the application of an AC signal, vibrates. A horn is closely mechanically coupled to the drivers. A tip, which functions as the energy applicator, extends distally from the horn. The vibrations of the drivers fosters like vibrations in the horn and, by extension, the tip. The motion of a vibrating tip against tissue results in the ablation of, the removal of, the tissue.

An inherent characteristic many powered surgical tool systems share with other electrically powered assemblies is that parasitic capacitances are present across the components of these systems. A parasitic capacitance is the capacitance present across two components that are at unequal voltages. A consequence of the presence of this capacitance is that a parasitic current can flow through one of the components. For example, when a handpiece includes a power generating unit to which AC drive signals are applied, due to the parasitic capacitance between the metal structural components of the handpiece and the power generating components internal to the handpiece through which current flows, a parasitic current can flow through the metal structural components. This parasitic current contributes to what is known as leakage current. Leakage current is the unintended flow of current through the components of a system to which a current is applied for other purposes.

The patient to which the handpiece of a powered surgical tool is, for safety reasons, considered to be tied to Earth ground. If a handpiece through which a leakage current could be present is applied to the patient, the leakage current can, in theory, flow through the patient to this ground. This current can adversely affect the functioning of the patient's own organs and tissue. This is why a surgical tool system with a handpiece intended for application to most the patient is typically designed to ensure that the normal leakage current flow is less than 100 µAmps. A surgical tool system with a handpiece intended for application to cardiac tissue must typically be designed so the normal leakage current flow is less than 10 µAmps. These requirements are based on the IEC 60601 Medical Design Standards. The IEC 60601 Standards also describe the process for testing a powered surgical tool to ensure the leakage current is below these maximum amounts.

It is still a further requirement that, for safety reasons, a tool applied to a patient cannot function as a connection to ground. This is so, if a voltage from another source is somehow applied to the patient, the tool will not function as a connection to ground that results in a current flow through the patient.

A number of methods are employed to reduce the flow of leakage current from a powered surgical handpiece. One method is to reduce the parasitic capacitance so as to reduce the parasitic current flow. If the tool is an ultrasonic handpiece, parasitic capacitance can be reduced by providing electrically insulating impedance disks between the drivers and the horn that the mechanical components of the handpiece that are intended to be vibrated by the drivers. A disadvantage associated with providing these disks is that they damp the transfer of vibrations from the drivers to the horn and tip. This mechanical damping reduces the efficiency of the handpiece.

A second method to reduce leakage current flow is to provide a matched current source. The matched current source applies a current to the low side conductors associated with the handpiece power generating unit. This matched current ideally is opposite and of equal magnitude to parasitic current present on the high side conductors. The matched current cancels out the parasitic current. The cancelation of the parasitic current ideally eliminates the contribution of the parasitic current to the leakage current. Leakage current consists primarily of the parasitic current. Accordingly, the cancelation of the parasitic current substantially eliminates the flow of leakage current from the handpiece through the patient.

A matched current source is formed from two components. A first one of these components is a supplemental winding integral with the transformer that is part of the control assembly. The second of these components is a capacitor distinct from the transformer.

The above type of assembly works reasonably well for providing a matched current source that provides a current for canceling out the leakage current that flows through the high side conductors. However, the present practice is to employ Y-type capacitor as the second component of the current source. The maximum voltage that can be allowed to develop across a Y-type capacitor is typically 250 VAC or less. The voltages present across the conductors of an ultrasonic handpiece can often exceed 1000 VAC. Therefore, it has proven difficult to prove a surgical tool system with ultrasonic drivers with a matched current source for reducing the magnitude of the leakage current.

Still another difficulty associated with providing a powered surgical tool system with a matched current source for reducing leakage current is that it can be difficult to adjust the current flow out of this current source. This can result in the tool system entering a state in which if the parasitic current and matched current are not substantially equal. If the handpiece enters this state, there is a chance that a leakage current above the tolerable levels will flow through a patient.

SUMMARY OF THE INVENTION

This invention relates to a new and useful power console for a surgical tool system. The power console serves as the assembly of the system that provides the drive signals to the power generating unit of the system. More particularly, the power console of the surgical tool system of this invention includes a transformer with a self-contained matched current source.

The power console of this invention includes a transformer that functions as the component of the console that outputs the drive signals applied to the power generating unit of the system handpiece. An input signal is applied to the primary winding of the transformer. The signal present across the secondary winding of the transformer is the drive signal.

The transformer also includes a matched current source. This matched current source produces a current that is substantially equal in magnitude and opposite in direction than the parasitic current present between the high side conductor over which the drive signals are applied to the power generating unit of the tool system. This matched current source includes a winding and a capacitor. The winding is referred to as the leakage control winding. One end of the leakage control winding is tied to ground. The capacitor is in series between the free end of the leakage control winding and the low side conductor.

Generally, the capacitor of the matched current source includes at least one layer of electrically conductive foil that is wrapped in around a winding of the transformer. This conductive wrap functions as one plate of the capacitor.

In some versions of the invention, the transformer includes a second conductive wrap disposed around the windings. This second wrap, in some species of the invention, functions as the second plate of the capacitor. In some species of this version of the invention, this second conductive wrap serves as a shield around the one or more windings around which this layer of electrically conductive material is wrapped.

In some versions of the invention, a portion of one of the windings also functions as the second plate of the capacitor of the matched current source. In some species of this version of the invention, at least a portion of the secondary winding functions as the second plate of the capacitor. In other species of this version of the invention, the leakage current winding functions as the second plate of the capacitor.

In some versions of the invention, the leakage current winding consists of a plurality of sub-windings. One or more switches tie the sub-windings together. This feature of the invention allows the voltage and, by extension, the current developed by the matched current source to, for a given voltage across the primary winding, be selectively set. This allows the level of the current sourced by the matched current source to be selectively set. This provides the ability to with an added degree of precision set the level of the current sourced by the matched current source during the manufacture of the console with which the transformer is integral so the current level is substantially equal to the parasitic current. In some constructions of the invention, this ability to set the level of the current sourced by the matched current source also makes it possible to use a single console to supply drive signals to handpieces which require drive signals of appreciably different frequencies.

In many versions of the invention, the transformer also includes a sense winding. The signal across the sense winding is employed by other components of the system as a signal that is representative of the voltage of the drive signals. In some versions of the invention in which the sense winding is present, the sense winding is connected to the leakage control winding.

Some powered surgical tool systems of this invention are ultrasonic tool systems. An ultrasonic tool system includes one or more drivers. Drivers are transducers that function as the power generating unit of the system. When an AC drive signal is applied to these drivers, they cyclically contract and expand. A tip is mechanically connected to these drivers. The expansion/contraction of the drivers induces a vibratory motion in the tip. The tip is applied to a tissue on the patient so the vibratory action causes the appropriate therapeutic effect on the tissue.

BRIEF DESCRIPTION OF THE DRAWINGS

The invention to which this application is directed is pointed out with particularity in the claims. The above and further features and benefits of this invention are understood from the following Detailed Description taken in conjunction with the accompanying drawings in which:

DETAILED DESCRIPTION

Figure 1:
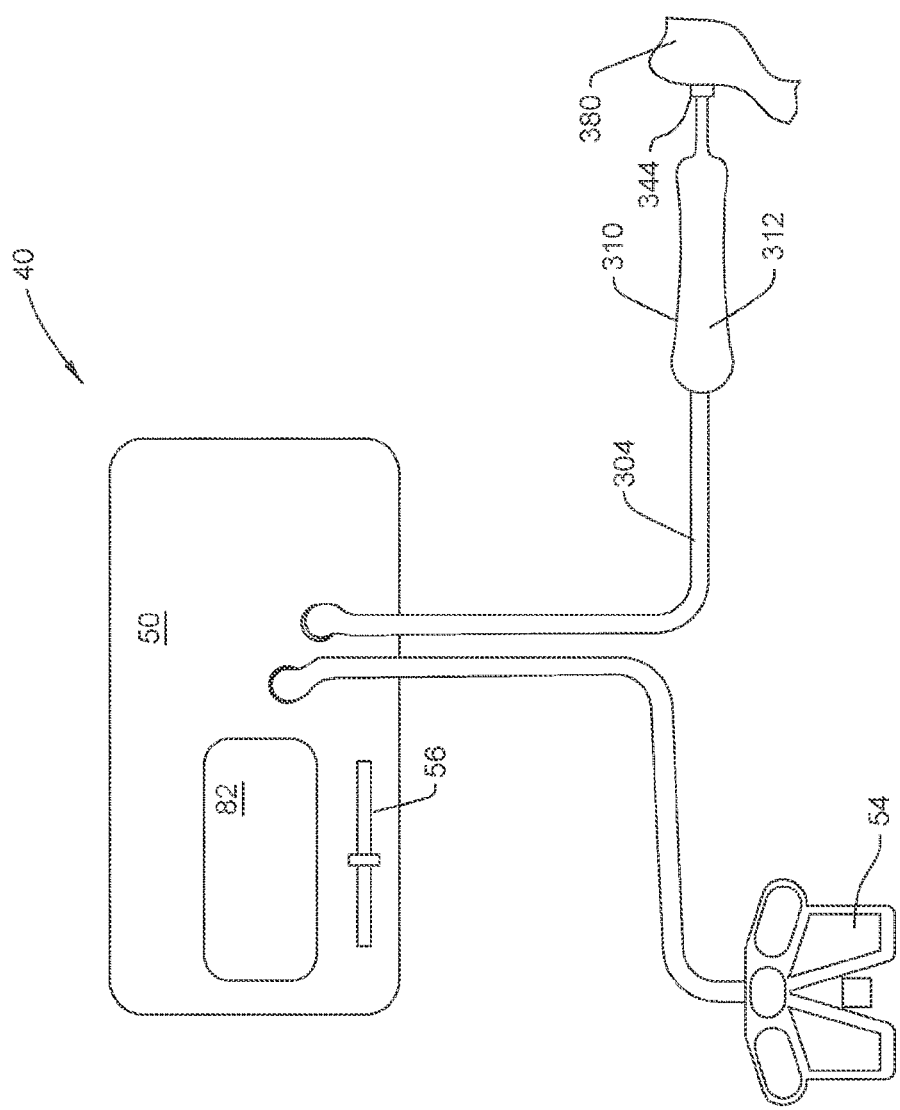
FIG. 1 depicts the basic components of a powered surgical tool system that includes the features of this invention.

A powered surgical tool system 40 of this invention is now generally described by reference to FIGS. 1 and 2. System 40 includes a handpiece 310. The handpiece 310 is an ultrasonic surgical tool. Accordingly, in this version of the invention system 40 can be described as an ultrasonic surgical tool system. Handpiece 310 includes a body or shell 312 that forms the proximal end of the handpiece. ("Proximal" is understood to mean towards the practitioner holding the handpiece, away from the site to which the handpiece is applied. "Distal" is understood to mean away from the practitioner, towards the site to which the handpiece is applied.) The body 312 is the portion of the handpiece 310 that is actually held by the medical practitioner.

One or more vibrating piezoelectric drivers 324 (four shown) are disposed inside shell 312. In FIG. 2 the handpiece shell 312 is not seen so the internal components of the handpiece 310 are exposed. Each driver 324 is formed from material that, when an AC voltage is applied to the driver, undergoes a momentary expansion or contraction. These expansions/contractions are on the longitudinal axis of a driver 324, the axis that extends between the proximally and distally directed faces of the driver. A pair of leads 328, only two leads seen in FIG. 2, extend away from each driver 324. The leads 328 are attached to the opposed proximally and distally directed faces of the drivers 324. Many, but not all handpieces 310, include piezoelectric drivers 324 that are disc shaped. These drivers 324 are arranged end to end in a stack. Leads 328 are the components of system 40 which the voltage, in the form of a drive signal, is applied to the drivers 324. In FIG. 2, drivers 324 are shown spaced apart from each other. This is for ease of illustrating the components. In practice, drivers 324 tightly abut.

The drivers 324 are understood to convert the electrical energy applied to the drivers to mechanical power. Accordingly, drivers 324 collectively function as the (mechanical) power generator of the system 40.

A post 330 extends longitudinally through drivers 324. The post 330 extends through the drivers 324 along the collinear longitudinal axes of the drivers. Not seen are through bores internal to the drivers 324 through which post 330 extends. Post 330 projects outwardly of both the most proximally located driver 324 and the most distally located driver 324.

A proximal end mass 320 is located adjacent the proximally directed face of the most proximally located driver 324. The exposed proximal end section of the post 330 is fixedly attached to mass 320. If post 330 is threaded, then mass 320 may be a nut.

A horn 334 extends forward from the distally directed face of the most distally located driver 324. While not shown, an insulating disc may be between the distal driver 324 and horn 334. Horn 334 has a proximal end base with a diameter approximately equal to the diameter of the drivers 324. Extending distally forward from the drivers 324, the diameter of the horn 334 decreases. The exposed distal end section of post 330 is affixed to the horn 334. If the post 330 is threaded, the horn base may be formed with a threaded bore (not identified) for receiving the post 330. Handpiece 310 is constructed so that the stack of drivers 324 is compressed between proximal end mass 320 and horn 334.

A tip 340 extends forward from the distal end of the horn 334. A coupling assembly, represented by a cylinder 336 extends forward from the horn 334. The coupling assembly removably holds the tip 340 to horn 334 and therefore the rest of the handpiece 310. The structure of the coupling assembly is not part of the present invention. Tip 340 includes an elongated stem 342. Stem 342 is the portion of the tip that, through the coupling assembly, is attached to the horn 334. Stem 342 extends forward of the handpiece shell 312. Tip 340 is formed to have a head 344 at the distal end of stem 342. Some tip heads 344 have smooth surfaces. Some heads 344 are formed with teeth 346. The geometry of the head 344 is not part of the present invention. Tip head 344 is the portion of the handpiece 310 applied to the site on the patient at which the procedure is performed. In FIG. 1, the tip head 344 is shown applied to a section of tissue 380.

Some tips heads 344 are provided with teeth designed to be applied directly to hard tissue, for example, bone. When this type of tip is reciprocated, the teeth cut the tissue in the same manner in which a conventional saw blade cuts tissue.

A sleeve 350, is typically disposed over tip stem 342. Sleeve 350 typically extends from a location near where the stem 342 is attached to the horn 334 to a location approximately 0.5 cm proximal to the head 344. Collectively, the handpiece 310, tip 340 and sleeve 350 are constructed so that the sleeve defines a fluid flow conduit that extends between the outer surface of the tip and the surrounding inner surface of the sleeve. The sleeve 350 has a fitting 352 adjacent the proximal end of the sleeve that extends to this conduit. The conduit is open at the distal end of the sleeve 350. When the handpiece 310 is in use, irrigating solution is flowed from the sleeve fitting, down the sleeve and discharged adjacent the tip head 344. In some versions of the system, the fluid serves as a medium through which the mechanical vibrations of the tip head are transferred to the tissue. This irrigating solution also functions as a heat sink for the thermal energy developed by the tip head as a consequence of the vibration of the head 344.

While not seen, the handpiece post 330, horn 334 and tip 340 are often formed with conduits. These conduits collectively define a fluid flow path from the tip head 344 to the proximal end of the handpiece 310. When handpiece 310 is in operation, suction is drawn through these conduits. The suction draws the irrigating fluid discharged through the sleeve 350 away from the site to which the tip is applied. Entrained in this irrigating fluid are debris generated as a result of the actuation of the tip 340. The suction also draws the tissue towards the tip head 344. The shortening of the distance between the tip head and the tissue improves the transmission of the mechanical vibrations from the tip head to the tissue.

A handpiece 310 of system 40 able to draw a suction is sometimes referred to as an aspirator or an ultrasonic aspirator.

Figure 3:
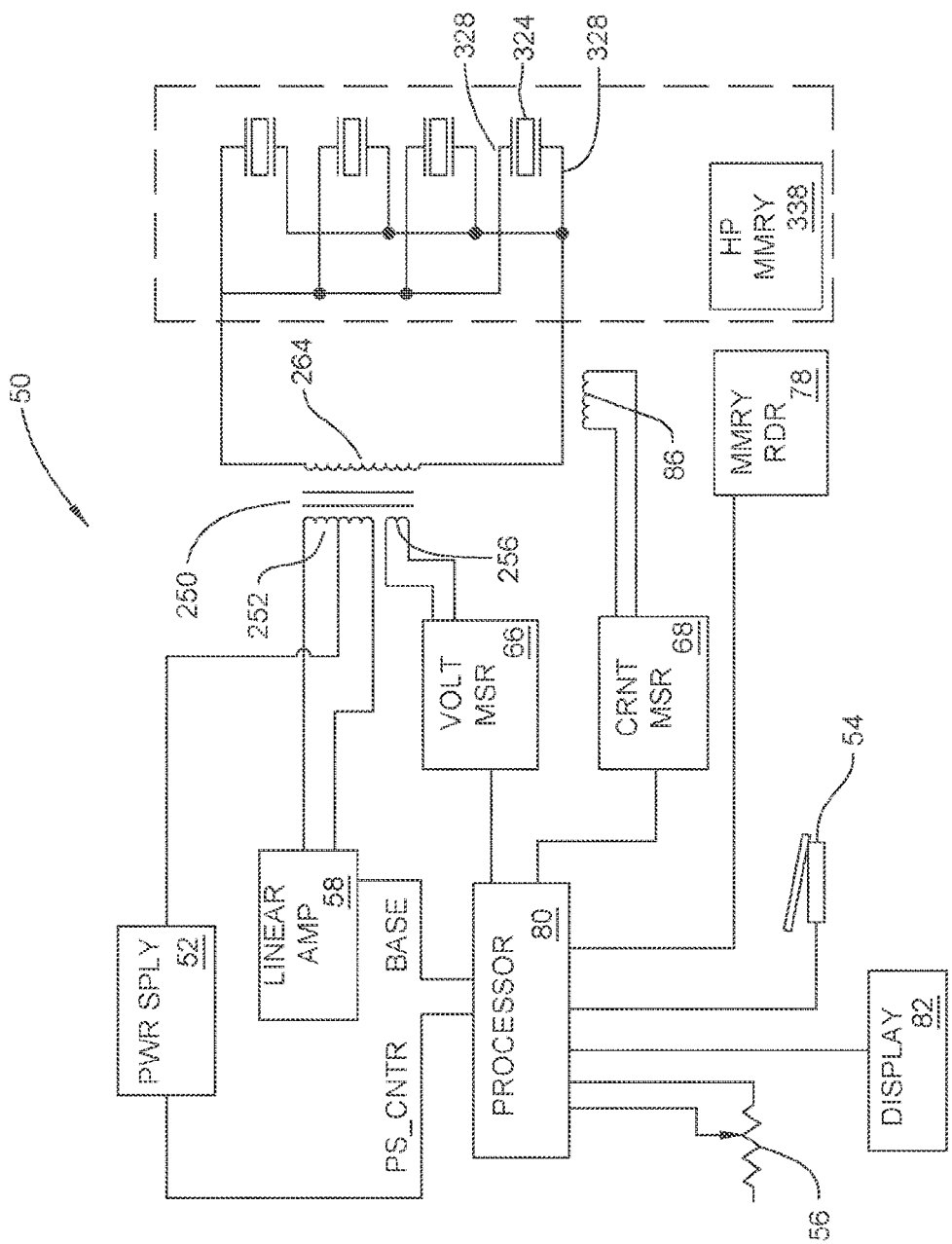
FIG. 3 is a block diagram of the basic electrical components of both the control console and handpiece of the system.

Handpiece 310 also includes a memory 338 seen as a block in FIG. 3. Memory 338, contains data describing the characteristics of the handpiece. Memory 338 may take the form of an EPROM, an EEPROM or an RFID tag. The structure of the memory is not part of the invention. The memory 338 contains data that identifies the handpiece 310. Memory 338 also contains data describing characteristics of the drive signal that can be applied to the handpiece drivers 324. Most handpieces 310 of this invention include a memory that, in addition to containing data capable of being read are able to store data written to the memory after manufacture of the handpiece 310. Ancillary components not illustrated are mounted to the handpiece to facilitate the reading of data from and the writing of data to the memory. These components consist of one or more of the following: conductors; exposed contacts/contact pins; a coil/antenna; or an isolation circuit.

Figure 2:
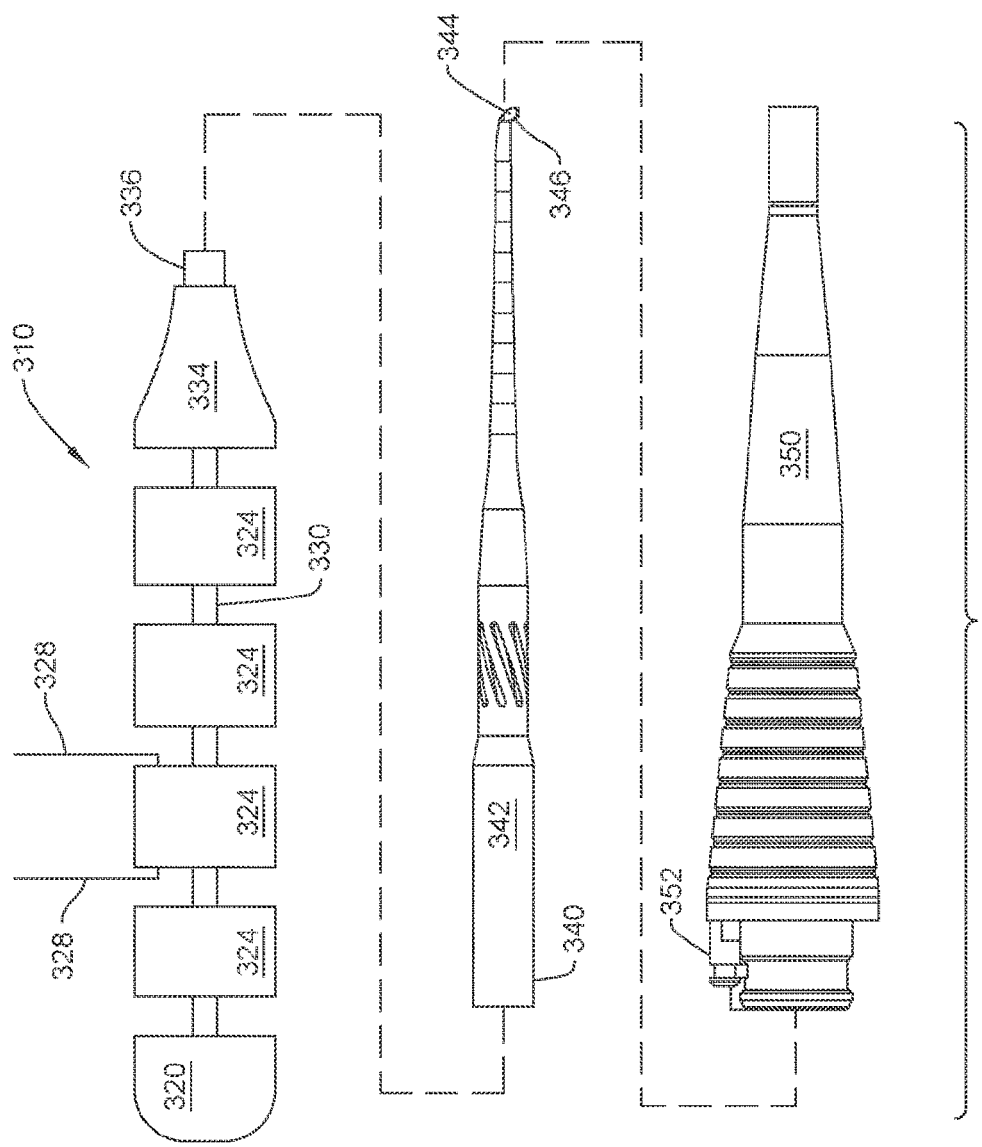
FIG. 2 is a diagrammatic depiction of the mechanical components of the tool, the handpiece, of the system.

A control console 50, now described by reference to FIGS. 1 and 3, is also part of system 40 of this invention. Control console 50 sources drive signals over a cable 304 to which handpiece 310 is connected. In versions of the invention in which the handpiece 310 is an ultrasonic handpiece, it is a common, but not required, to assemble cable 304 and handpiece 310 as a single unit. The drive signals are applied to the drivers 324. At any given instant, the same drive signal is applied to each driver 324. The application of the drive signals causes the drivers to simultaneously and cyclically expand and contract. A stack of drivers 324 is often between 1 and 5 cm in length. The distance, the amplitude, of movement over a single expansion/contraction cycle of the drivers may be between 1 and 10 microns. Horn 334 amplifies this movement. Consequently, the distal end of the horn 334 and, by extension, tip head 344, when moving from the fully contracted position to the fully extended position, moves typically a maximum of 1000 microns and often 500 microns or less. Some tips 340 are further designed so the longitudinal extension/retraction of the tip stem 342 also induces a rotational movement in the head 344. This rotational movement is sometimes referred to as a torsional movement. When handpiece 310 is actuated to cause the cyclic movement of the tip, the head 344 is considered to be vibrating.

The components internal to the control console 50, generally seen in FIG. 3, includes a power supply 52. Power supply 52 outputs a DC voltage the level of which can be set. This voltage is typically between 25 and 250 VDC. The voltage of the signal out of the power supply 52 is set based on a POWER_SUPPLY_CONTROL (PS_CNTRL) signal applied to the power supply. The signal output by power supply 52 is applied to the center tap of the primary winding 252 of a transformer 250. The opposed ends of transformer primary winding 252 are tied to a linear amplifier 58. Amplifier 58 applies AC signals that vary in both potential and frequency to the ends of the transformer primary winding 252. A BASE signal applied to amplifier 58 as a control signal regulates the frequency and potential of the signals output by the amplifier 58. In versions of the invention in which system 40 includes an ultrasonic handpiece 310, the AC signal that is developed across the primary winding has a frequency between 10 kHz and 100 kHz. This signal has a peak to peak voltage of at least 200 Volts and more preferably, at least 300 Volts.

The structure of the power supply 52 and the linear amplifier 58 is not part of the present invention. A further understanding of these sub-assemblies can be found in PCT Pat. App. No. PCT/US2016/031651, the contents of which are contained in WO 2016/183084 A1/US Pat. Pub. No. 2018/0056328 A1, both of which are explicitly incorporated herein by reference.

The AC signal developed across the primary winding 252 of transformer 250 induces an AC signal across the secondary winding 264 of the transformer 250. This signal across the secondary winding of transformer 250 is the drive signal applied over cable 304 to the handpiece drivers 324. In versions of the invention in which the drive signal is used to actuate ultrasonic drivers the drive signal typically has a voltage of at least 500 VAC and often at least 1000 VAC.

Transformer 250 includes a sense winding 256. Sometimes, sense winding 256 is referred to as tickler coil. The voltage of the signal present across sense winding 256 is applied to a voltage measuring circuit 66. Based on the signal across sense winding 256, circuit 66 produces a signal representative of $V_s$ the magnitude and phase of the potential of the drive signal across the drivers 324. A coil 86, also disposed in control console 50, is located in close proximity to one of the conductors that extends from the transformer secondary winding 264. The signal across coil 86 is applied to a current measuring circuit 68. Circuit 68 produces a signal that represents the magnitude and phase of current $i_s$, the current of the drive signal sourced to the handpiece drivers 324.

The signals representative of the voltage and current of the drive signal applied to handpiece 310 are applied to a processor 80 also internal to the control console 50. Control console 50 also includes a memory reader 78. Memory reader 78 is capable of reading the data in handpiece memory 338. The structure of memory reader 78 complements the handpiece memory 338. Thus, memory reader can be: an assembly capable of reading data in a EPROM or EEPROM or an assembly capable of interrogating and reading data from an RFID tag. In versions of the invention in which the data read from the memory 338 are read over the conductors over which the drive signal is sourced to the handpiece 310, the memory reader 78 may include an isolation circuit. Data read by reader 78 are applied to processor 80.

Connected to control console 50 is an on/off switch. In FIGS. 1 and 3, the on/off switch is represented by a foot pedal 54. The state of pedal 54 is monitored by processor 80. The on/off switch is the user actuated control member that regulates the on/off state of the system 40. In FIG. 1, foot pedal 54 is shown as being part of a foot pedal assembly that includes plural pedals. The added pedals may be used to control devices such as irrigation pump, a suction pump or a light. These supplemental devices are not part of the present invention.

Control console 50 is shown as having a slide switch 56. Like foot pedal 54, the state of switch 56 is monitored by processor 80. Switch 56 is set by the practitioner to control the magnitude of the amplitude of the vibrations of tip head 344. Foot pedal 54 and switch 56 are understood to be general representations of the means of entering on/off and amplitude setting commands to system 40. In some constructions of the system a single control member may perform both functions. Thus the system 40 may be configured so that when a lever or foot pedal is initially first depressed, the system causes tip head to undergo a vibration cycle that is of relatively small amplitude. As a result of the continued depression of the lever or foot pedal, the control console resets the drive signal applied to the handpiece so as to cause tip head 344 to undergo vibration cycles that are of a larger magnitude.

A display 82 is built into control console 50. The image on display 82 is shown as being generated by processor 80. Information depicted on display 82 includes information identifying the handpiece and possibly the tip and information describing characteristics of the operating rate of the system. Display 82 may be a touch screen display. In these versions of the invention, by depressing images of buttons presented on the display 82 command can be entered into processor 80. Not shown are interface components between the display 82 and the processor 80 that facilitate the presentation of images on the display and the entry of commands into the processor.

The processor 80 regulates the outputting of drive signals from the control console 40. The practitioner-controlled inputs upon which the processor 80 sets the drive signals are the state of the on/off pedal 54 and the state of the slide switch 56. Commands entered through the display 82 may also be used to control the setting of the drive signal. The characteristics of the drive signal are also set based on data read from the handpiece memory 338. The characteristics of the drive signals are also employed by the console as feedback signals that further contribute to the setting of the drive signal. Based on these plural inputs, processor 80 outputs the signals that control the drive signal. These signals are the POWER_SUPPLY_CONTROL signal applied to power supply 52 and the BASE signal applied to amplifier 58.

Figure 4:
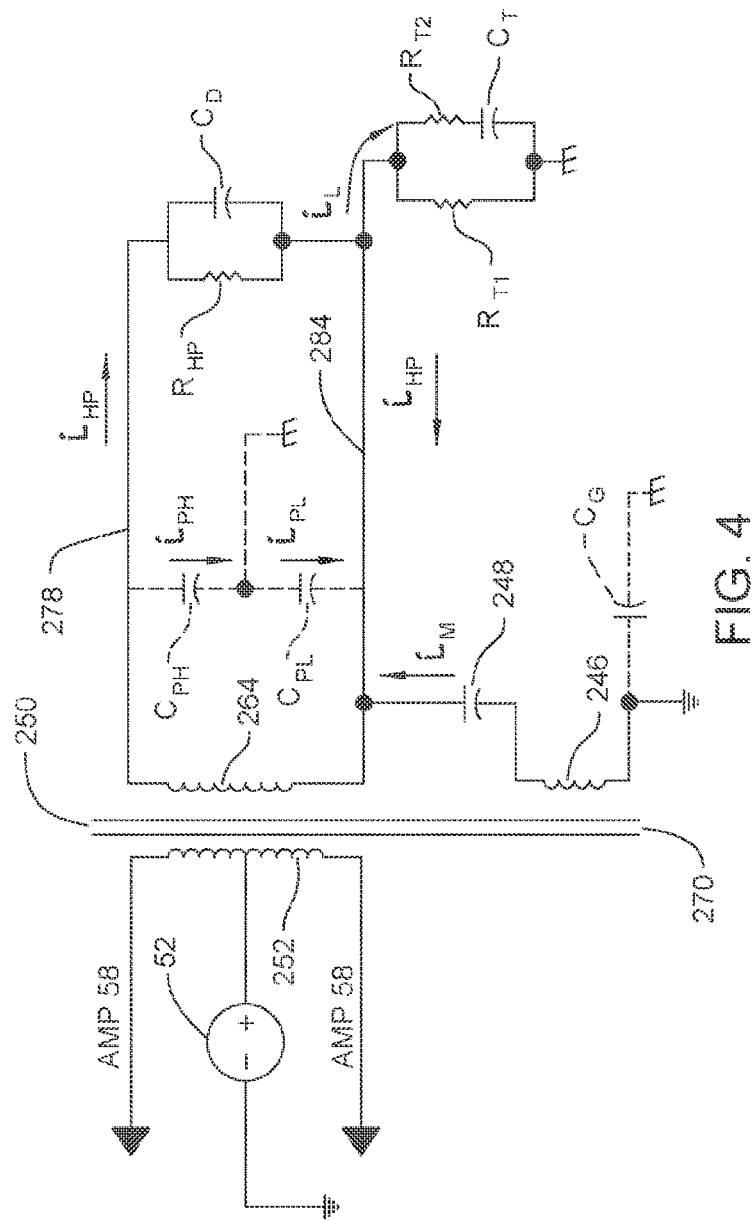
FIG. 4 is a schematic diagram of the transformer internal to the control console, the handpiece and the patient to which the handpiece is applied.

An understanding of the theory of operation of transformer 250 of this invention is obtained by reference to FIG. 4. FIG. 4 is a schematic depiction of the electrically active components of the transformer 250 as well as the components to which the drive signal produced by the components are applied. The transformer is thus shown has having a core 270. To the left of the core 270, the transformer 250 is seen as including the primary winding 252. From FIG. 3 it is understood that the opposed ends of the primary winding 252 are connected to linear amplifier 58. The voltage output by power supply 52 is applied to the center tap of the primary winding 252. To reduce drawing complexity, sense winding 256 is not seen in FIG. 4.

The secondary winding 264 is shown directly opposite the primary winding 252 on the right side of core 270. In FIG. 4, the drivers 324 are represented as their electrical equivalent, a capacitor $C_D$. A resistor $R_{HP}$ is shown in parallel with capacitor $C_D$. Resistor $R_{HP}$ represents the mechanical equivalent of impedance of the handpiece 310 and tip 340. This impedance may actually have resistive component, a capacitive component and an inductive component. Conductor 278 represents the high side conductors internal to the console 50, cable 304 and the handpiece 310 that connect secondary winding 264 to the drivers 324. Conductor 284 is the low side conductor, the return conductor, between the drivers 324 and the secondary winding 264. Current flows to and from the secondary winding 264 to the drivers is current $i_{HP}$. Current $i_{HP}$ is a function of the voltage of the drive signal and the impedance of both the handpiece, the impedance the parallel circuit of capacitor $C_D$ and mechanical equivalent of impedance $R_{HP}$.

Also seen in FIG. 4 is what is considered a circuit representative of the human body for leakage current analysis and testing. This circuit is based on the standards contained in IEC 60601. This circuit consists of a parallel circuit with two branches. A first branch of the circuit is a resistor $R_{T1}$. The second branch of the model is a second resistor $R_{T2}$ in parallel with a capacitor $C_T$. In this model, the surgical tool is applied to one end of this circuit. The opposed end of the circuit is considered connected to Earth ground. To prevent damage to the tissue, the current flow from the surgical instrument to the tissue, the leakage current $i_L$ through this circuit should be zero. Since the current $i_{HP}$ is a result of the drive signal, this current all flows from the high side conductor 278, through the drivers 324 and back through the low side conductor. Current $i_{HP}$ therefore does not contribute to the leakage current $i_L$.

The circuit over which the drive signal is applied from the secondary winding 264 to the drivers 324 also has a parasitic capacitances. These capacitances are represented as series connected capacitors $C_{PH}$ and $C_{PL}$. Capacitors $C_{PH}$ and $C_{PL}$, the conductors and ground to which they are connected are shown as dashed components because they do not physically exist in circuit. The junction of capacitors $C_{PH}$ and $C_{PL}$ is connected to Earth ground. Capacitor $C_{PH}$, the capacitor connected to the high side conductor 278, represents the parasitic capacitance between the high side conductor and Earth ground. Capacitor $C_{PL}$, the capacitor connected to the low side conductor 284, represents the parasitic capacitance between the low side conductor 284 and Earth ground.

The presence of these parasitic capacitances causes a parasitic current flow through the electrically conductive components of the system 40. Specifically, the parasitic current through capacitor $C_{PH}$ is parasitic current $i_{PH}$. The parasitic capacitance through capacitor $C_{PL}$, results in existence of parasitic current $i_{PL}$. If the parasitic currents flow through the low side conductor 284, these currents would form components of the leakage current $i_L$. Again, to prevent damage to tissue, it is understood that current $i_L$ should be zero or at least as close to zero as possible.

To prevent the flow parasitic current through the low side conductor 284, internal to transformer 250 is a variable matched current source. This current source produces a matched current $i_M$ that is applied to the low side conductor 284 that is equal in magnitude and opposite in direction to the current $i_{PH}$, the current that exists owing to the high side capacitance $C_{PH}$. The application of this matched current $i_M$ has two effects on the flow of parasitic current over conductor 284 to the tissue 380. First, since the matched current $i_M$ is equal to or substantially equal to parasitic current $i_{PH}$, the extent to which parasitic current $i_{PH}$ contributes to the presence of the current $i_L$ applied to the tissue is reduced, if not substantially eliminated. For the purposes of this invention, matched current $i_M$ is considered substantially equal to parasitic current $i_{PH}$, if the matched current cancels out the parasitic current to the extent necessary to result in a leakage current that is below the standards for the system with which the transformer 250 is integral. When the transformer 250 is contained within a console 50 that is part of a surgical tool system 40 that must meet the IEC 60601 body floating standards, the matched current is considered substantially equal to the parasitic current if the matched current is within 100 μAmps of the parasitic current $i_{PH}$. When the transformer 250 is contained within a console 50 that is part of a surgical tool system 40 that must meet the IEC 60601 cardiac floating standards, the matched current is considered substantially equal to the parasitic current if the matched current is within 10 μAmps of the parasitic current $i_{PH}$.

The presence of the matched current $i_M$ also has an effect on the low side parasitic current $i_{PL}$. Specifically, since the matched current $i_M$ is substantially equal to the high side parasitic current $i_{PH}$, the voltage across parasitic capacitor $C_{PL}$ is substantially zero. As a result of this voltage equalization, there is little, if any low side parasitic current $i_{PL}$ to contribute to the leakage current $i_L$ through the tissue 380.

The matched current consists of two components, a leakage control winding 246 and a capacitor 248 both of which are integral to the transformer 250. Winding 246 is referred to as the leakage control winding because the parasitic current substantially, if not entirely, comprises the leakage current $i_L$. One end of the leakage control winding 246 is tied to ground. Capacitor 248 is connected in series between the free end of the leakage control winding 246 and the low side conductor 284. The voltage across the winding 246 varies with the voltage across the primary winding 252. Accordingly, the matched current source formed by winding 246 and capacitor 248 can be considered a variable voltage source.

In FIG. 4, the ground of the console is shown connected to Earth ground. This connection is through capacitor $C_g$. Capacitor $C_g$ represents the parasitic capacitance between the console and Earth ground.

Figure 5:
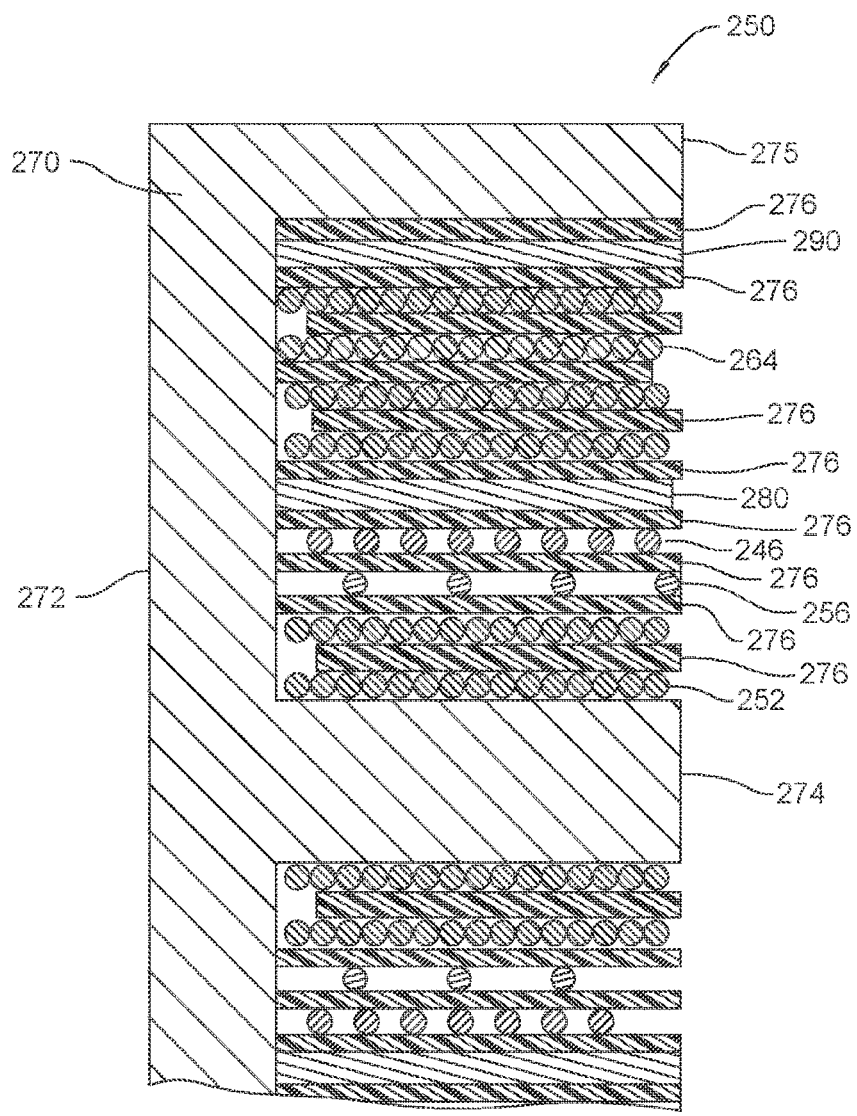
FIG. 5 is a cross sectional view of a first transformer of this invention.

FIG. 5 illustrates the structure of a basic transformer 250 of this invention. Transformer 250 is formed from an E-shaped core 270 formed from ferrite. The core 270 is shaped to have a base 272. Three parallel legs extend outwardly from the base 272. A first leg, center leg 274, extends outwardly from the center of the base 272. Transformer 250 is understood to be symmetric around the longitudinal axis, the horizontal axis in FIG. 5, through the center leg 274. Outer legs 275, one shown, extend outwardly from the opposed ends of the base. Windings 246, 252, 256 and 264 are wrapped around the center leg 274 and contained within the perimeter of the circle defined by the opposed inner surfaces of the outer legs 275.

Transformer 250 is constructed so the winding closest to the core center leg 274 is the primary winding 252. In the illustrated version of the invention, the primary winding 252 is shown as having two layers of turns. The layers of turns are separated by a dialectic, insulating wrap 276. As discussed below, transformer 250 includes plural insulating wraps 276. Wraps 276 are formed form a polyethylene terephthalate resin sheet. One such resin is sold under the trademark Mylar by Dupont Teijin Films. This wrap has a thickness of at least 0.005 mm and often a thickness of at least 0.008 mm. The wrap 276 between the layers of turns forming the primary winding 252 is shown as not extending to base 272 of the core 270. This is to represent that the layers of turns forming the primary winding 252 are connected together. The insulating layer 276 located over the outer layer of primary winding 256 is shown as extending across the whole of the length of the space defined by the core in which the windings are disposed. This is to represent that the primary winding is isolated from the next outwardly adjacent winding.

The sense winding 256 is the winding disposed immediately over the primary winding 252. Sense winding 256 has the fewest turns of any of the windings. This is why, in FIGS. 5, 7 and 9 the sense winding 252 is shown as consisting of a single layer of turns that includes relatively few individual turns. In many versions of the invention, the relative direction of the turns of the windings must be properly set in order to ensure that the transformer 250 properly functions. Transformer 250 of FIG. 5 is constructed so the turns of the sense 256 winding are in the same direction as the turns of the primary winding 252.

An insulating layer 276 that extends over the sense winding 256.

The leakage control winding 246 is the winding that is disposed over the sense winding 256. In many versions of the invention, the leakage control winding 246 consists of more turns of wire than the sense winding 256 and less turns of wire than the primary winding 252. The turns of wire forming the leakage control winding are wrapped around the core center leg 274 in the direction opposite in which the wire turns forming the primary winding 252 are wrapped. An insulating layer 276 extends over the leakage control winding 246.

An inner conductive wrap 280 extends around the insulating layer 276 disposed over the leakage control winding 246. Wrap 280 is formed of electrically conductive material such as copper and has a thickness of at least approximately 0.002 mm and often at least 0.003 mm. This wrap 280 as well as the below described conductive wraps 288 and 290 are non-shorting. This means the opposed ends of the wrap should not be connected together. An insulating layer 276 is disposed over the conductive wrap 280.

Figure 7:
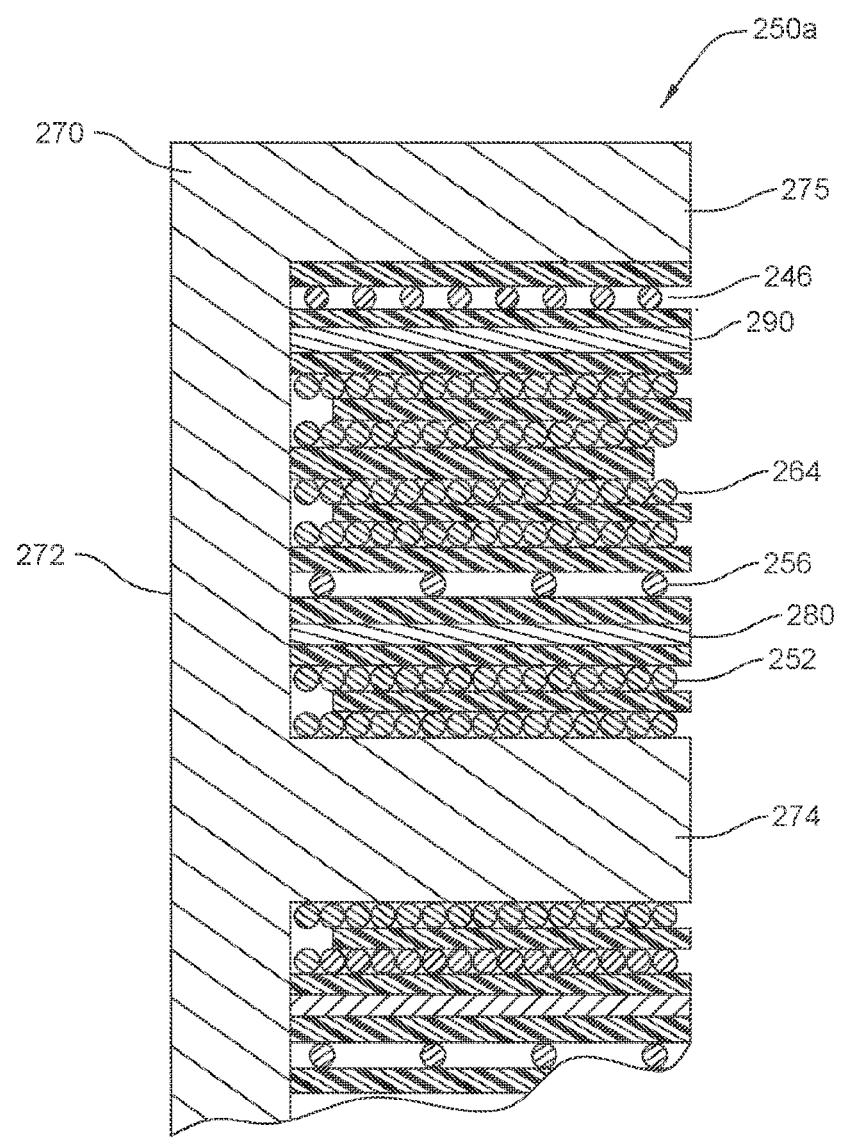
FIG. 7 is a cross sectional view of a second transformer of this invention.
Figure 9:
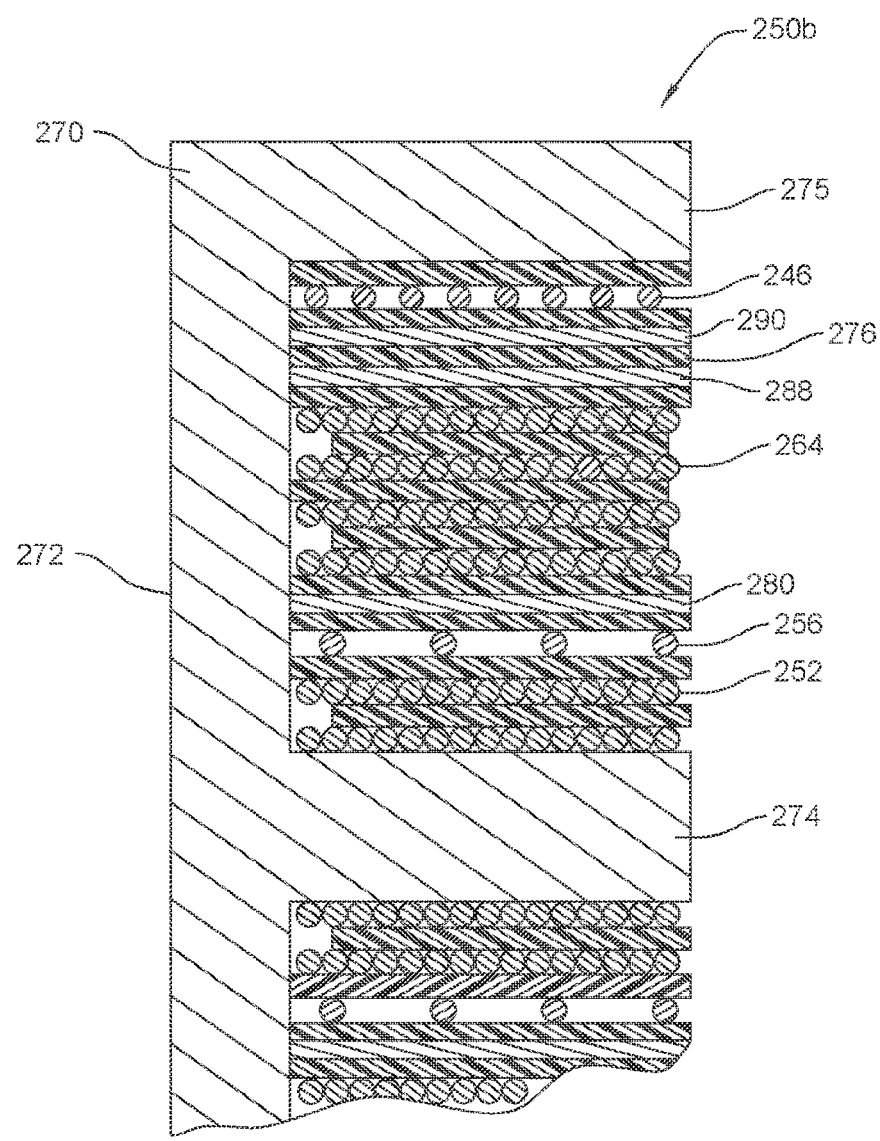
FIG. 9 is a cross sectional view of a third transformer of this invention.

Secondary winding 264 is the winding disposed over the insulating layer 276 disposed over inner conductive wrap 280. The secondary winding typically has the most individual turns of wire as well as the most layers of turns of the windings of transformer 250. In FIGS. 5, 7 and 9, this is symbolically illustrated by the secondary winding 264 having four layers of turns. Transformer 250 is formed so the turns of the secondary winding are wrapped around the core center leg 274 in the direction opposite the direction in which the turns of the wire forming the primary winding 252 are wrapped. Insulating layers 276, one layer identified, that do not extend between the complete length of the space within the core in which the windings are disposed are shown interleaved with the turns of secondary winding 264.

Console 50 is configured so that the terminal end of the wire forming the end of the inner most layer of turns of the secondary winding is the terminal end of the secondary winding that is connected to the low side conductor 284. Secondary winding 264 of transformer 250 is wound around core center leg 274 in a direction opposite the direction in which the primary winding 252 is wound.

An insulating layer 276 is shown disposed over the whole of the length of the outermost layer of turns of the secondary winding 264.

A second conductive wrap, wrap 290, is disposed over the insulating layer 276 disposed over the secondary winding 264. An insulating layer 276 is disposed over the second conductive wrap 290.

Figure 6:
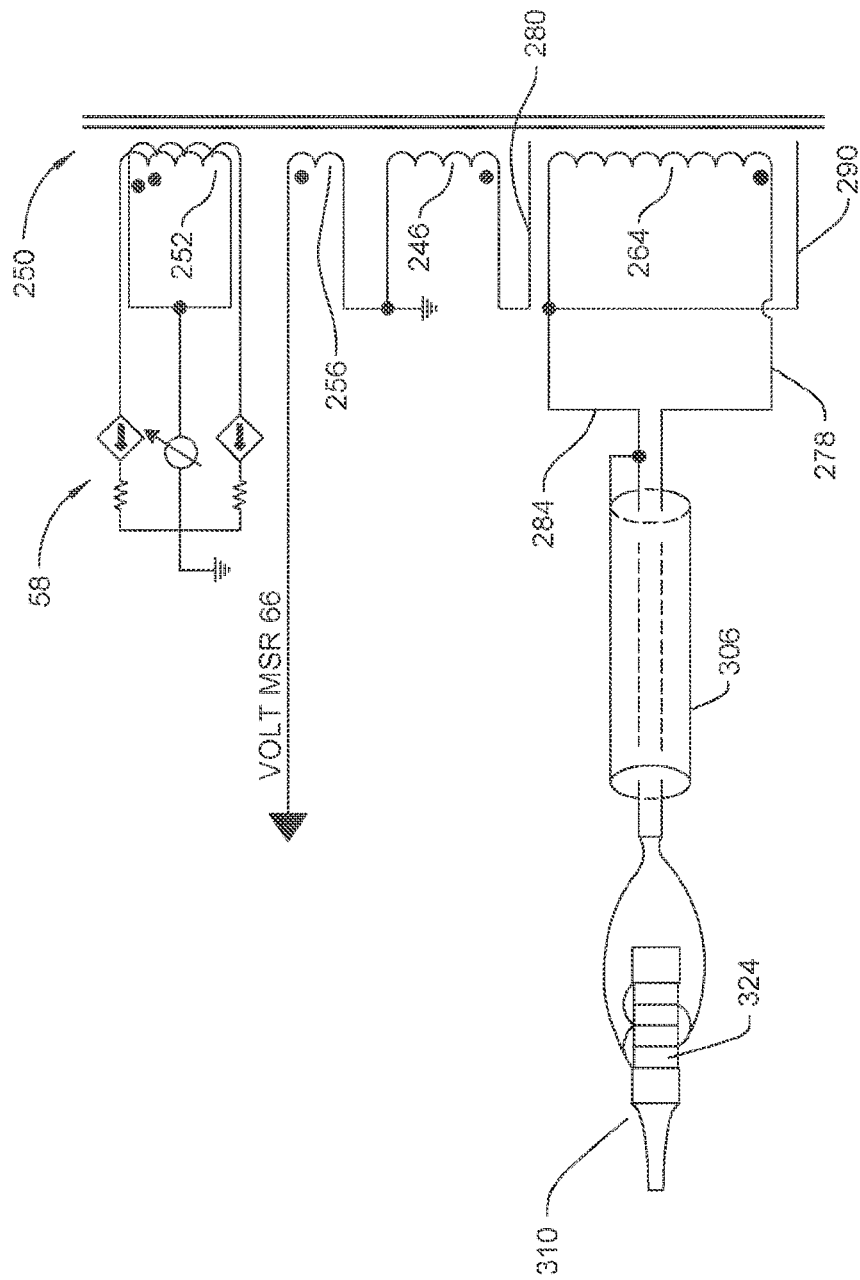
FIG. 6 is a schematic depiction of the transformer of FIG. 5.

An understanding of the electrical connections between the windings of the transformer 250 is obtained by reference to FIG. 6. In FIG. 6 and companion FIGS. 8 and 10, the primary winding 252 is shown as it actually constructed, as a bifilar winding. One end of each of the bifilar winding is connected to the variable power supply 52. The opposed ends of each bifilar winding is shown connected to the linear amplifier 58, schematically represented as two current sinks.

One end of the sense winding 256 is tied to an end of the leakage control winding 246. These two common winding ends are tied to ground. The free end of the sense winding 256 is the end of the winding attached to the voltage measuring circuit 66. The free end leakage control winding 246, the high side of winding 246, is connected to the inner conductive wrap 280.

Outer conductive wrap 290 is connected to the end of the secondary winding 264 that is connected to the low side conductor 264. The outer conductive wrap 290 thus serves as an electromagnetic shield around the outside of the transformer windings.

In FIGS. 5, 7, and 9, the low side conductor 284 is shown connected to a shield 306. This shield 306 is internal to cable 304. The high side conductor 278 is shown extending through the shield 306.

When system 40 of this invention is actuated, the control console 50 causes an AC voltage to appear across the primary winding 252. The electromagnetic field that develops as a result of this voltage induces voltages in the other windings 246, 256 and 264. The voltage induced in secondary winding 264 is applied to the handpiece drivers 324 as the drive signal. The voltage that appears across the sense winding 256 is applied to the voltage measuring circuit 66 as a measure of the voltage of the drive signal.

The voltage that is developed across the leakage control winding 246 is applied to the inner conductive wrap 280. This wrap is within 2 mm and, more preferably, within 1 mm of the adjacent inner wrap of the turns of wire forming the secondary winding 264. Inner conductive wrap 280 is separated from these adjacent turns of the secondary winding 264 by the insulating layer 276 located between these wire wraps. Thus, the inner conductive wrap 280, the adjacent wrap of turns the secondary winding and the insulating layer 276 between these wraps function as the capacitor 248 of the matched current source of system 40. Ideally, the components forming the system are constructed so the current produced by this current source is equal and opposite to current $i_{PH}$ that exists as a result of the high side parasitic capacitance. The cancellation of this leakage current $i_{PH}$ reduces, if not eliminates, the flow of leakage current $i_L$ from the system into the tissue.

A further feature of transformer 250 of this invention is that the voltage across capacitor 248 can exceed 500 Volts and, more preferably, at least 1000 Volts without causing a breakdown of the capacitor or the transformer itself. This means transformer 250 can output a drive signal across the secondary winding 264 that is at least 500 Volts and, more preferably, at least 1000 Volts. Drive signals having these voltage are necessary to power the power generating units of certain powered surgical tools such as the ultrasonic handpiece 310 of the described system 40.

FIG. 7 illustrates the structure of an alternative transformer 250a, that can be incorporated into a control console 50 of the system 40 of this invention. To minimize redundancy, the identification numbers associated with the sections of the core, the windings and insulating layers associated with alternative transformer 250a and the below described alternative transformers 250b and 250c will be the same where these components are identical with the components of transformer 250. Also, to minimize redundancy, and drawing complexity, the insulating layers 276 between the layers of the primary windings and the layers of the secondary windings are not identified in FIGS. 7 and 9.

Transformer 250a, is constructed to have the primary winding 252 wrapped closest to the center leg 274 of the core 270 as in the first embodiment of the invention. An insulating layer 276 is disposed over the outer layer of the primary winding. The inner conductive wrap 280 is disposed over the insulating layer 276 that surrounds the primary winding.

The inner conductive wrap 280 is surrounded by an insulating layer 276. The sense winding 256 is wrapped around the insulating layer 276 wrapped around the inner conductive wrap 280. The turns of the wire forming the sense winding 256 are wrapped in the same direction of the turns of the wire forming the primary winding 252.

The secondary winding 264 is wrapped around the insulating layer 276 disposed over the sense winding 256. Transformer 250a is constructed so the turns of the wire forming secondary winding 264 are wrapped in the direction that is opposite the direction in which the turns of the wire forming the primary winding are wrapped. An insulating layer 276 is disposed over the outer layer of the turns forming of the secondary winding.

The outer conductive wrap 290 is disposed over the insulating layer 276 disposed over the secondary winding 276. An insulating layer 276 is disposed over the outer conductive wrap 290.

The leakage control winding 246 is disposed over the insulating layer that surrounds the outer conductive wrap 290. Transformer 250a is formed so the turns of the leakage control winding 246 are wrapped in opposite direction than the turns of the primary winding 252 are wrapped. An insulating layer 276 is wrapped around the leakage control winding 246 so as to form the outer skin of the winding sub-assembly integral with transformer 250a.

Figure 8:
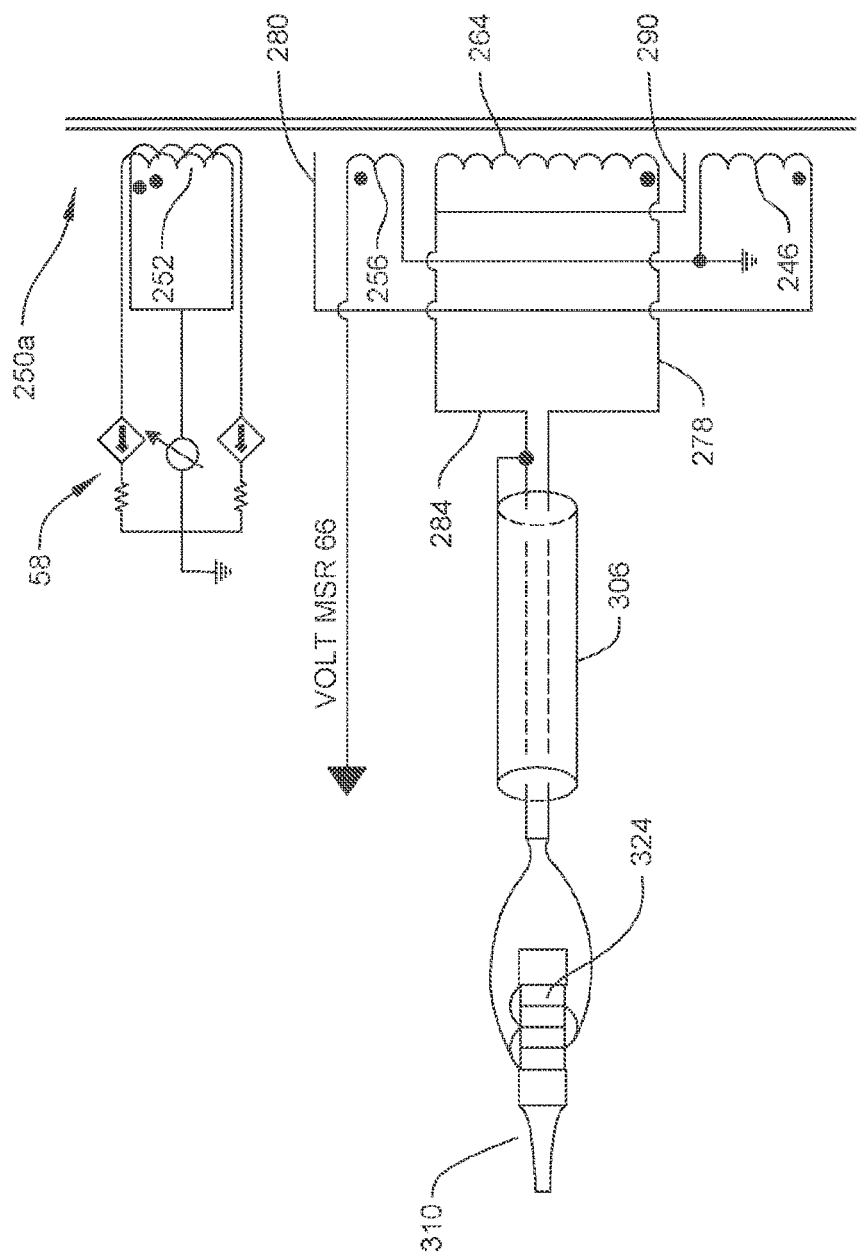
FIG. 8 is a schematic depiction of the transformer of FIG. 7.

Transformer 250a, as can be appreciated from FIG. 8, is constructed so that inner conductive wrap 280 is connected to the high side terminal of the leakage control winding 246.

The low side of the leakage control winding 246 is tied to ground. Also tied to ground is the low side of sense winding 256. The high side of the sense winding is connected to the voltage measuring circuit 66.

Outer conductive wrap 290 is connected to the low side of secondary winding 264. The low side of the secondary winding 264 is also connected to the shield 306 internal to cable 304.

Transformer 250a is constructed so that inner conductive wrap 280 functions as one plate of capacitor 248. The second plate of capacitor 248 is the inner most layer of turns of secondary winding 264. The dielectric layer of capacitor 248 consists of the insulating layers 276 located around the opposed sides of the sense winding 256. In this version of the invention, the sense winding 256 is disposed between the two components of the transformer 250a that form the capacitor 248. The voltage across the sense winding 256 is relatively low, typically 5% or less the voltage across the secondary winding 264. By extension the electric field developed around sense winding 256 is also relatively low. Accordingly, the presence of the sense winding 256 between the two components of transformer 250a that form capacitor 248 does not appreciably affect the function of the capacitor 248. This means the capacitor 248, even with sense winding 256 disposed between the plates of the capacitor, is, in combination with the leakage control winding 246, able to produce a current that substantially matches parasitic current $i_{PH}$.

Outer conductive wrap 290 serves as a shield around the windings 252, 256 and 258 disposed within the wrap 290.

This versions of transformer 250a operates in the same general way the first transformer 250 operates. As a result of an AC signal being applied to the primary winding 252, the drive signal develops across the secondary winding 264. A voltage also is developed across the leakage control winding 246. This voltage, when applied through capacitor 248, to the low side conductor 284 results in the presence of current on the low side conductor that is equal and opposite to the parasitic current that develops between the high side conductor and Earth ground. This matched current reduces if not eliminates the extent to which this parasitic current contributes to the leakage current is applied to the tissue to which the handpiece is applied.

A further feature of transformer 250a is that the leakage control winding 246 is the outermost winding of the transformer. This means that after all the other windings are in place, the transformer can be placed in a test fixture. By applying voltages across the primary winding and measuring the current through and voltages across the test fixture, a determination can be made regarding how many turns of wires should be used to construct the leakage control winding to ensure that the current produced by the matched current source as closely as possible matches the high side leakage current.

A second alternative transformer 250b of this invention is now initially described by reference to FIG. 9. Transformer 250b is constructed so that, as with transformer 250, the primary winding 252 is the winding located closest to the core center leg 272. An insulating layer 276 is disposed around the primary winding 252. The sense winding 256 is wrapped around the insulating layer 276 wrapped around the primary winding 252. Sense winding 256 is wrapped in the same direction in which the primary winding 252 is wrapped. An insulating layer 276 is wrapped around the sense winding 256.

The inner conductive wrap 280 is disposed over the insulating layer 276 disposed around the sense winding 256.

An insulating layer 276 is disposed around the sense winding 256. The secondary winding 264 is disposed over the insulating layer 276 disposed over the sense winding 256. Transformer 250*b* is constructed so that secondary winding 264 is wrapped in the same direction as primary winding 252. An insulating layer 276 is disposed over the secondary winding 264.

An intermediate conductive wrap 288 is disposed over the insulating layer 276 wrapped around the secondary winding 264. An insulating layer 276 is disposed over the intermediate conductive wrap 288. The outer conductive wrap 290 is disposed over the insulating layer 276 disposed over the intermediate conductive wrap 288. An insulating layer 276 is disposed over the outer conductive wrap 290.

The leakage control winding 246 is disposed over the insulating layer that surrounds the outer conductive wrap 290. Leakage control winding 246 is wrapped in the same direction around the core center leg in which the primary winding 252 is wrapped. An insulating layer 276 is wrapped around the leakage control winding 246 so as to form the outer skin of the winding sub-assembly integral with transformer 250*b*.

Figure 10:
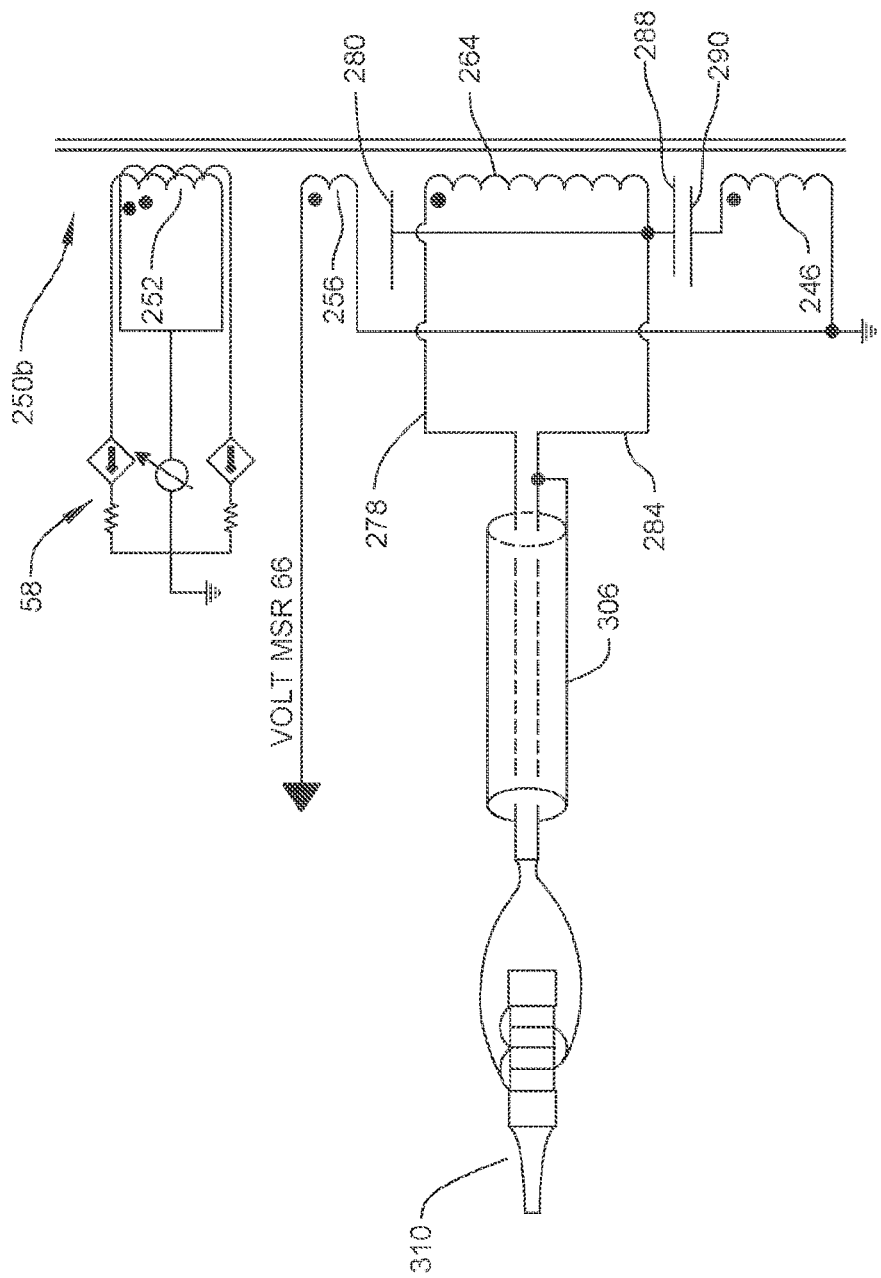
FIG. 10 is a schematic depiction of the transformer of FIG. 9.

As seen by reference to FIG. 10, transformer 250*b* is constructed so the inner conductive wrap 280 and intermediate conductive wrap 288 are both tied to the low side of transformer secondary winding 264. Wraps 280 and 288 thus collectively form one plate of capacitor 248. The outer conductive wrap 290 is tied to the high side of the leakage control winding 246. Outer conductive wrap 290 thus forms the second plate of capacitor 248 in transformer 250*b*. The insulating layer 276 between the conductive wraps 288 and 290 functions as a portion of the dielectric layer of capacitor 248.

Transformer 250*b* is this constructed so that both plates of the capacitor 248 are formed from conductive wraps. One of the plates, the plate tied to the secondary winding 264 is actually formed two conductive wraps, wraps 280 and 288. Accordingly, in comparison to the capacitors 248 of transformers 250 and 252*a*, the capacitor 248 of transformer 250*b* has a higher capacitance. This makes it possible to reduce the size of the leakage control winding while still providing a matched current source that produces a current substantially equal to parasitic current $i_{PH}$.

Figure 11:
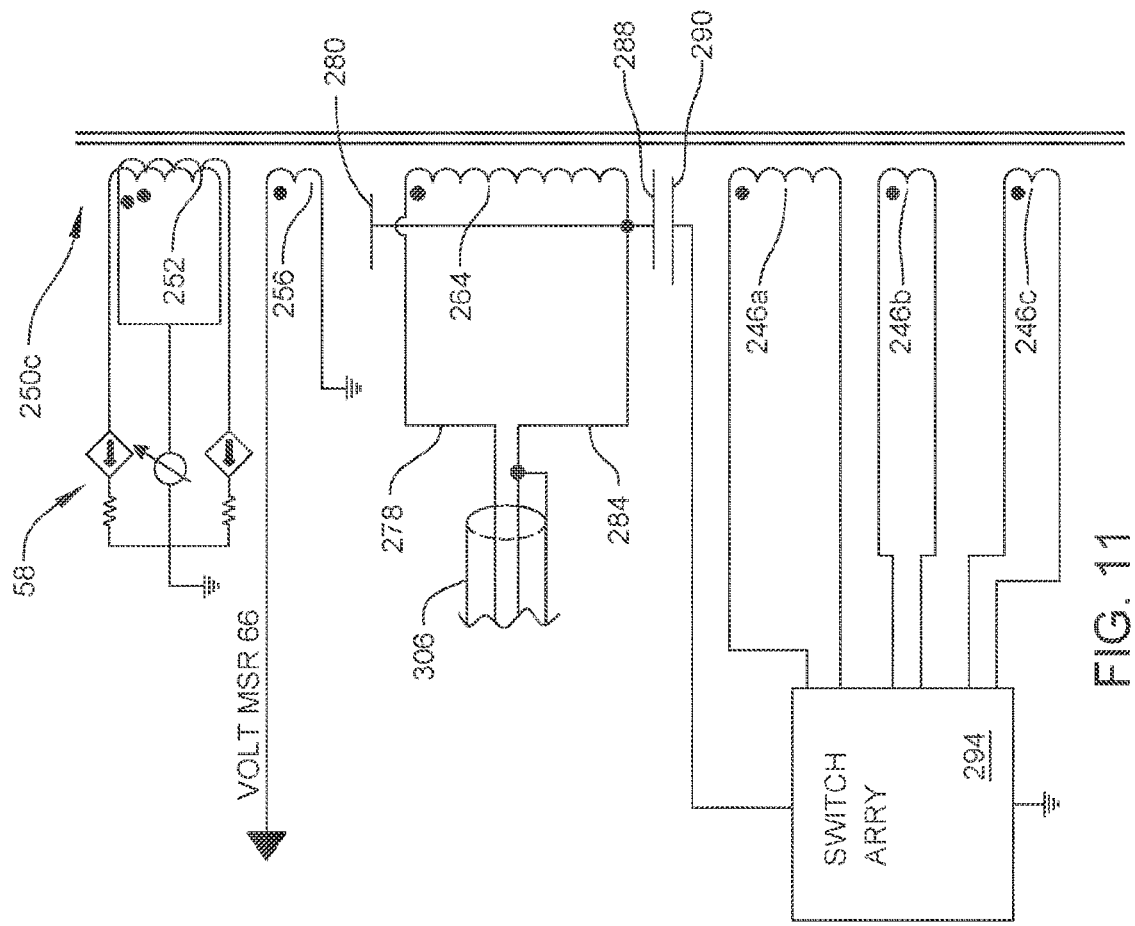
FIG. 11 is a schematic depiction of a fourth transformer of this invention.

FIG. 11 is a schematic diagram of a third alternative transformer, transformer 250*c*, that may incorporated into system 40 of this invention.

Transformer 250*c* is provided with the previously described windings 252, 258 and 264 and conductive wraps 280, 288 and 290. The windings 252, 258 and 264 and conductive wraps 280, 288 and 290 of transformer 250*c* are arranged in the same order relative the center leg 274 of core 270 as the identical windings and conductive wraps of transformer 250*b*.

A difference between transformers 250*b* and 250*c* is that, instead of a single leakage control winding, transformer 250*c* has three transformer control sub-windings 246*a*, 246*b* and 246*c*. Physically, sub-windings 246*a*, 246*b* and 246*c* windings are located in the same positioned relative to windings 252, 256 and 264 that the single winding 246 is located relative the same windings in transformer 250*b*. In some, but not all versions of the invention, the turns of wire forming the leakage control windings 246*a*, 246*b* and 246*c* occupy the same number of layers of winding turns as the single leakage control winding 246*a*.

As can be seen from FIG. 11, the high side of the sense winding 256 is connected to the voltage measuring circuit 66. The low side of sense winding 256 is connected to ground. Both the inner and intermediate conductive wraps 280 and 288, respectively, are tied to the low side of secondary winding 264.

Integral with transformer 250*c* is a switch array 294. Switch array 294 may physically be attached to or separate from the transformer 250*c*. The opposed ends of each of the sub-windings 246*a*, 246*b* and 246*c* are connected to the switch array 294. Also connected to the switch array 294 is the outer conductive wrap 290. Switch array 294 also has a connection to ground. Internal to switch array 294 are a number of switches, not illustrated. The switch internal to the switch array are configured to: connect the high side of any one of the sub-windings 246*a*, 246*b*, 246*c* to the outer conductive wrap 290; connect the low side of the sub-windings to the high sides of the outer windings; and to connect the low side of any one of the sub-windings to ground.

Transformer 250*c* is, like transformer 250*b*, constructed so that conductive wraps 280 and 288 function as one place of capacitor 248. Conductive wrap 290 functions as the second plate of capacitor 248.

Transformer 250*c* is further formed so that by the selective setting of switches forms the switch arrays 294, 296. By selectively setting the switches of switch array 294 any one of the sub-windings 246*a*, 246*b* or 246*c*, any combination of two of the sub-windings or all three sub-winding may be connected between the outer conductive wrap 290 and ground. This means any one, two or all of the sub windings 246*a*, 246*b* and 246*c* can function as the leakage control winding of the matched current source. This feature of the invention facilitates the adjustment of the matched current source of transformer 250*c* to ensure that the current $i_M$ output by the source is substantially equal to the current that is present as a result of the high side parasitic capacitance $C_{PH}$. This adjustment process is typically performed after the transformer 250*c* is assembled or after the transformer 250*c* is fitted to the rest of the console 50.

The above is directed to specific version of the invention. Alternative versions of the invention may have features different from what has been described.

For example, the features of the different versions of the invention may be combined. Thus the leakage control sub-windings 246*a*, 246*b*, 246*c* and switch array 294 of transformer 250*c* may be incorporated into transformers 250, 250*a* and 250*b*.

In versions of the invention where there are plural leakage control windings that are selectively tied together to form the matched current source, there may be two or four or more individual windings.

The structures of the components forming the invention may also differ from what has been described. For example, some versions of the invention may include a transformer with an E/I core assembly, a U core assembly, a U/I core assembly or an I core.

In some versions of the invention, it may not be necessary to provide the transformer with an internal sense coil.

Other assemblies for forming capacitor 248 integral with the matched current source are also possible. Thus, in some versions of the invention, a conductive wrap may be attached to the low side of the secondary winding 264. This conductive wrap may be in sufficient proximity to the a portion of the high side of the leakage control winding 246 that the conductive wrap serves as one plate of capacitor 248 and a section of the leakage control winding serves as the second plate of capacitor 248.

Likewise, there is no requirement that in all versions of the invention, the console be constructed so that, the AC voltage is developed across the transformer primary winding by applying a voltage to a center tap of this winding and cyclically connecting the opposed ends of the winding to ground. In alternative versions of the invention, an AC voltage source may be the source of the AC signal that is applied to the opposed ends of the transformer primary winding 252. Likewise, in all constructions of the invention, depending of the particular use of the transformer, the AC voltage applied or induced across the transformer may be constant.

While in most versions of the invention, the transformer will have at least one conductive wrap, there is no requirement that in all versions of the invention the transformer include plural conductive wraps. When a single conductive wrap is present, this wrap typically, but not always, forms one plate of capacitor 248 of the matched current source. If three conductive wraps are present, there is no requirement that each wrap form part of the capacitor 248. Two of the wraps may form a plate or the plural plates of the capacitor 248; the third wrap is a shield. Likewise, transformers with four or more plates are within the scope of this invention. Thus it is within the scope of this invention that a transformer include five conductive wraps, specifically and assembly where: two wraps form a first plate of capacitor 248; two wraps form a second plate of capacitor 248; and a single wrap functions as a shield around the outer windings of the capacitor.

Likewise, the order of the windings 246, 252, 256 and 264 relative to the center of the core 270 vary from what has been described.

Not all features may be present in all versions of this invention. For example an alternative console of this invention may include a matched current source that is not wholly built into the transformer. In some versions of the invention the transformer may contain the set of leakage current windings 246a, 246b and 246c as well as the switches that selectively connect the windings together. In these versions of the invention the capacitor 248 integral with the matched current source may be separate from the transformer 250

While not shown it is understood that in some embodiments of these versions of the invention, transistors, typically FETs may function as the individual switches of the switch array 294.

In regard to this feature of the feature of providing the matched current source with plural leakage current windings that are selectively connected together it should be understood there is no requirement that there always be three sub-windings that can potentially be selectively connected together. In in some versions of the invention there may only two sub-windings. In still other versions of the invention there may be four or more sub-windings that can be selectively connected together. Further there may be constructions of the invention wherein one of the plural sub-windings is always a sub-winding of the leakage control winding.

In most versions of the invention the conductive wrap that functions as a capacitor plate extends circumferentially around, 360° around, the underlying transformer winding or windings. In some versions of the invention, this conductive layer may not extend completely around the underlying winding or windings. Alternatively, the conductive wraps may extend more than 360° around the windings. It should be understand that regardless of the extent to which the wrap extends around the windings, the opposed sides of the wrap should not be electrically connected to each other. This is to prevent the conductive wrap from shorting out.

It should likewise be understood that powered surgical tools to which versions of the console of this invention supply a drive signal are not limited to tools where the power generating unit comprises a set of ultrasonic transducers. Other systems of this invention may be constructed to the tool power generating unit is a device that emits light (photonic energy). Another system of this invention may include a handpiece with a either a monopolar or bipolar electrode assembly. In this type of system, the conductors that extend through the handpiece can be considered the power generating unit. The electrode or electrodes that are applied to tissue would be the energy application. This type of system operates by applying current to the tissue. The current heats the tissue to cause the intended ablation of or cauterization of the tissue.

Further the control console of this invention as well as the transformer of this invention may be used for purposes other than applying an AC signal with a relatively low leakage current to a device other than a powered surgical handpiece. Such devices to which include bipolar forceps. In this type of assembly, the tips of the forceps may be considered the energy applicator of the handpiece. The conductors integral with the arms of the forceps over which the AC signal is applied to the tips may be considered the power generating unit of the handpiece.

Accordingly, it is the object of the appended claims to cover all such modifications and variations that come within the true spirit and scope of the invention.

What is claimed is:

1. A control console for supplying a drive signal to the power generating unit of a surgical tool, said console including:
   a transformer with a primary winding across which an AC voltage is applied; and a secondary winding across which a drive signal is induced so the drive signal can be applied to the power generating unit of the surgical tool; and
   a matched current source comprising a leakage control winding across which the AC voltage that is present across the primary winding induces a voltage and a capacitor connected between the leakage control winding and the transformer secondary winding, the matched current source designed to produce a current that at least partially cancels a leakage current present in the drive signal as a result of parasitic capacitance, wherein both the leakage control winding and the capacitor of the matched current source are internal to the transformer.

2. The control console of claim 1, wherein:
   a set of turns of one of the windings of the transformer functions as a plate of the matched current source capacitor.

3. The control console of claim 2, wherein a set of turns of the secondary winding functions as the plate of the matched current source capacitor.

4. The control console of claim 1, wherein the transformer comprises a layer of conductive material wrapped around the windings of the transformer and that is connected to a low side of the transformer secondary winding so as to function as a shield.

5. The control console of claim 1, wherein a sense winding for determining a voltage of the drive signal is disposed in the transformer.

6. The control console of claim 5, wherein the sense winding is located between the primary winding and the secondary winding.

7. The control console of claim 5, wherein: the leakage control winding is located outwardly of said sense winding and the secondary winding is located outwardly of the leakage control winding.

8. The control console of claim 5, wherein the sense winding is connected to the leakage control winding.

9. The control console of claim 5, wherein the leakage control winding is the outermost winding of the transformer.

10. The control console of claim 1, wherein the leakage control winding is located outwardly of the primary winding.

11. The control console of claim 1, wherein the leakage control winding is located outwardly of the secondary winding.

12. The control console of claim 1, wherein:
the primary winding has a center tap to which a DC voltage is applied; and
opposed ends of the primary winding are tied to a circuit that selectively ties the ends of the primary winding to ground so as to cause the AC voltage to develop across the primary winding.

13. The control console of claim 1, wherein:
the leakage control winding consists of a plurality of sub-windings; and a set of switches selectively connect said sub-windings of said leakage control winding together so as to, for a given voltage across the primary winding set the voltage that develops across the leakage control winding.

14. The control console of claim 1, wherein the leakage control winding is the outermost winding of the transformer.

15. The control console of claim 1, wherein the capacitor has a voltage rating of greater than 500 volts.

16. The control console of claim 1, comprising:
a high side conductor and a low side conductor each connected to a different end of the secondary winding and the power generating unit of the surgical tool for applying the drive signal induced across the secondary winding to the power generating unit of the surgical tool; and
a cable connected to the control console and the surgical tool, the cable including a portion of the high side conductor, a portion of the low side conductor, and an internal shield through which the portion of the high side conductor extends, wherein the low side conductor is electrically coupled to the internal shield.

17. The control console of claim 16, wherein the matched current source is coupled to the low side conductor and configured to produce a current that is substantially equal to a parasitic current present on the high side conductor.

18. The control console of claim 16, wherein the portion of the low side conductor extends through the internal shield.

19. The control console of claim 16, wherein the cable and the surgical tool are assembled as a single unit, the cable being removably connectable to the control console to form the high side conductor and the low side conductor.

20. A transformer for supplying a drive signal to a power generating unit of a surgical tool, the transformer including:
a primary winding for receiving an AC voltage;
a secondary winding for inducing the drive signal applied to the power generating unit of the surgical tool; and
a matched current source comprising a leakage control winding across which the AC voltage that is present across the primary winding induces a voltage and a capacitor connected between the leakage control winding and the transformer secondary winding, the matched current source designed to produce a current that at least partially cancels a leakage current present in the drive signal as a result of parasitic capacitance,
wherein a set of turns of one of the windings of the transformer functions as a plate of the matched current source capacitor.

21. A transformer for supplying a drive signal to a power generating unit of a surgical tool, the transformer including:
a primary winding for receiving an AC voltage;
a secondary winding for inducing the drive signal applied to the power generating unit of the surgical tool, the secondary winding including a high side end and a low side end for supplying the drive signal to the power generating unit of the surgical tool;
a leakage control winding across which the AC voltage that is present across the primary winding is configured to induce a voltage for producing a current that at least partially cancels a leakage current present in the drive signal as a result of parasitic capacitance; and
a layer of conductive material connected to the low side end of the secondary winding and wrapped around the primary winding, secondary winding, and the leakage control winding so as to function as an electromagnetic shield.

* * * * *